United States Patent [19]

Welch

[11] Patent Number: 5,468,211

[45] Date of Patent: Nov. 21, 1995

[54] INTERNAL RING RELEASING DEVICE FOR A VACUUM CONSTRICTION SYSTEM

[75] Inventor: Daniel P. Welch, Zimmerman, Minn.

[73] Assignee: Mentor Corporation, Santa Barbara, Calif.

[21] Appl. No.: 132,646

[22] Filed: Oct. 6, 1993

[51] Int. Cl.$^6$ ............................................. A61F 5/00
[52] U.S. Cl. ............................................. 600/38; 600/39
[58] Field of Search ......................... 128/842, 844, 128/918; 604/347–353; 600/38, 39, 40

[56] References Cited

U.S. PATENT DOCUMENTS

| | | | |
|---|---|---|---|
| 1,117,618 | 11/1914 | Ach | 600/38 |
| 3,631,853 | 1/1972 | Burdette | 600/38 |
| 3,744,486 | 7/1973 | Wilson | 600/38 |
| 4,378,008 | 3/1983 | Osbon | 600/38 |
| 5,020,522 | 6/1991 | Stewart | 600/38 |
| 5,083,556 | 1/1992 | Osbon | 600/39 |
| 5,115,800 | 5/1992 | Matajevic | 600/39 |
| 5,125,890 | 6/1992 | Merrill | 600/39 |
| 5,195,943 | 3/1993 | Chaney | 600/38 |

Primary Examiner—Michael A. Brown
Attorney, Agent, or Firm—Larkin, Hoffman, Daly & Lindgren, Ltd.

[57] ABSTRACT

An internal ring releasing device including a housing, a cylindrical adaptor at one end, piston within the housing and a primary insert in the other end of the housing. The piston includes a constriction ring groove for holding a constriction ring. The piston is caused to move from a load position with a constriction ring to an unload position where the constriction ring slides off around the base of an erect penis.

10 Claims, 17 Drawing Sheets

INTERNAL RING RELEASING DEVICE FOR A VACUUM CONSTRICTION SYSTEM

BACKGROUND OF THE INVENTION

1. Field of the Invention

The present invention is for a vacuum constriction system, a medical device, and, more particularly, pertains to an internal constriction ring releasing device (IRRD) for a vacuum constriction device system (VCD).

2. Description of the Prior Art

The market for vacuum constriction systems in the United States is currently $20 Million and growing. The projected market is $30 Million by fiscal year 1998.

All systems currently on the market operate similarly in the sense that the constriction ring is applied from the outside of the cylinder.

The successful use of a vacuum constriction system requires a certain amount of practice. The most difficult part of using the system involves maintaining the vacuum, especially during the transfer of the ring from the outside of the cylinder onto the base of the penis. Patients who do not become proficient at this lose a significant amount of vacuum during this transfer and this affects the quality of their erection.

The present invention overcomes the disadvantages of the prior art by providing a system which releases the ring from the inside and eliminates the outside transfer step, and thus, there is no potential for vacuum loss during ring transfer. The system is easy to use. The quality of the erection is better, resulting in increased user satisfaction and co-user satisfaction.

SUMMARY OF THE INVENTION

The general purpose of the present invention is an internal ring releasing device ("IRRD") accessory for a vacuum ("VCS" or "VCD") constriction system that allows a constriction ring to be released onto an erect penis from the inside of the system rather than from the outside of the cylinder. The accessory can be used with other vacuum constriction systems on the market.

According to one embodiment of the present invention, there is provided an internal ring releasing device for a vacuum constriction system, including a housing, a cylindrical adaptor at one end, a piston within the housing and a primary insert at the other end of the housing where the piston includes a constriction ring groove for supporting a constriction ring adjacent to the primary insert. The piston is in a load position and moves into an unload position when a vacuum is created in the vacuum constriction system. The piston can also be caused to move by releasing a mechanism, whether the mechanism be a vent hole, an elastomeric valve, a mechanical valve, all O-rings can be used at appropriate positions to provide for an airtight seal between the components. Springs can also be utilized within the cylindrical housing in conjunction with the piston so as to gauge the degree of vacuum release of the constriction ring depending upon the vacuum drawn by the vacuum constriction device.

Significant aspects and features of the present invention are set forth below.

The system allows the user to manually and easily release the constriction ring at any point he desires during the use of the system.

The ring is easy to load, especially for patients who may have limited manual dexterity.

The internal diameter of the open end pressing against the body is not too large when using the system and creates an airtight seal without pulling scrotum into the system. Once the ring is loaded, the internal diameter of the ring is about 5.7 cm. The internal diameter of the open end that surrounds the ring and presses against the body is about 7.5 cm. This end is about 0.5 to 0.7 cm. thick and rounded for patient comfort.

The system is also useable with other vacuum constriction systems on the market using a preferred ring for the IRRD.

The system cleans up with soap and water.

The IRRD system can be sold with any vacuum constriction systems or by itself for other VCS's or VCD's.

Having thus described embodiments of the present invention, it is one object hereof to provide an internal ring releasing device for a vacuum constriction system where a constriction ring is released either via manual direction or automatically around the base of the penis providing for a quality erection.

One object of the present invention is an internal ring releasing device for vacuum constriction system which is easily utilized and requires very little manual dexterity. The constriction ring is stretched about a constriction ring groove on the moveable piston.

Another object of the present invention is an internal ring releasing device which can be used with any vacuum constriction system, although a cylinder adaptor may be required to accommodate different designs by different manufacturers.

A further significant aspect and feature of the present invention is an internal ring releasing device which is easy to utilize, effective and provides for a quality penile erection.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
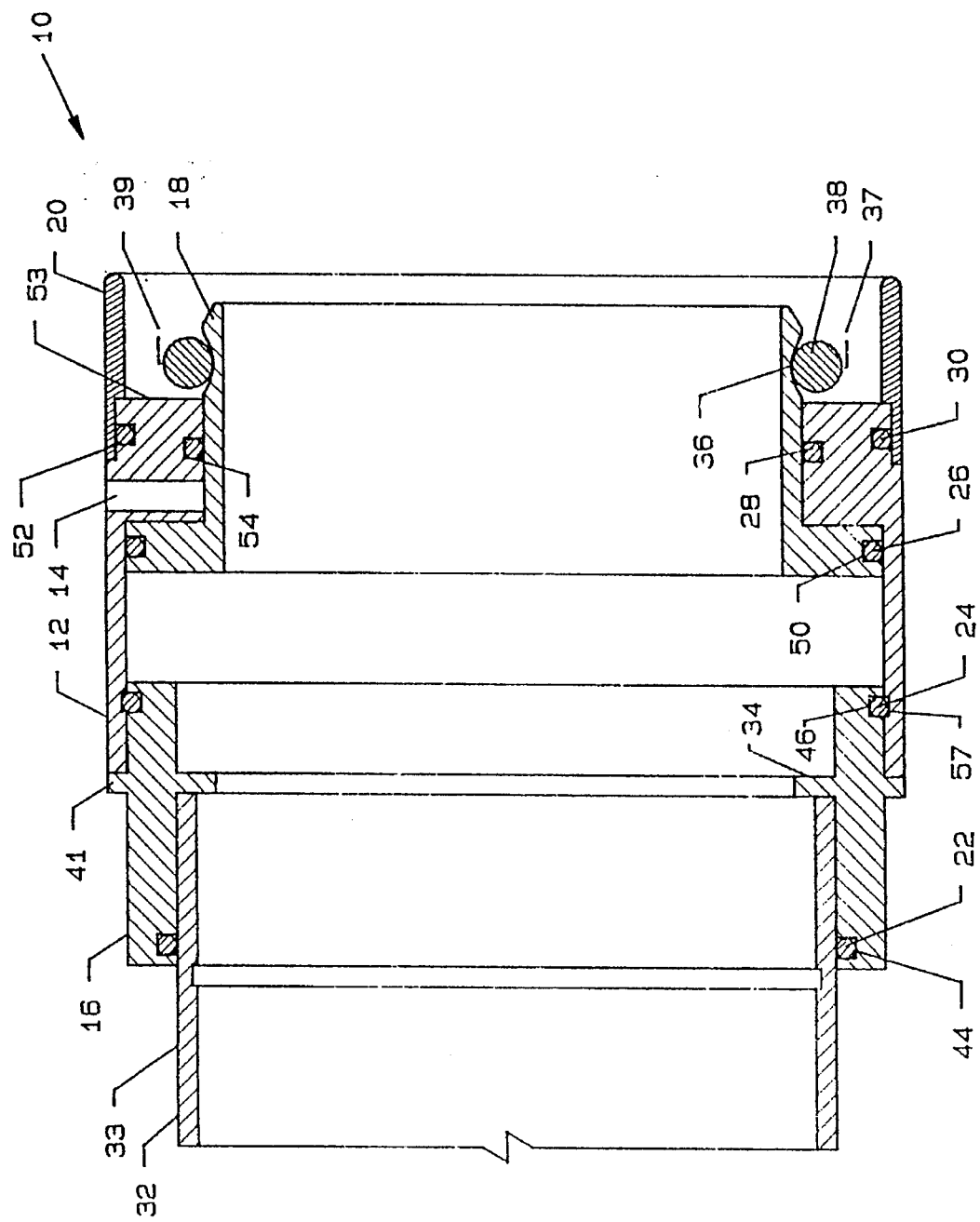
FIG. 1 illustrates a cross sectional view of an internal ring releasing device, the present invention.

FIG. 1 illustrates a cross sectional view of the internal ring releasing device 10, present invention, including a housing 12, including a vent 14 in the housing 12, a cylinder adaptor 16, a piston 18, and a optional primary insert 20, all of which are later described in detail. A plurality of optional O-rings 22, 24, 26, 28 and 30 provide for an airtight seal. A cylinder 32 of a vacuum constriction system or vacuum constriction device having an outer surface 33 engages into the cylinder adaptor 16 and seats against a rim 34 in the cylinder adaptor 16. A groove 36, on the piston 18, receives a constriction ring 38 with ears 37 and 39. The ears 37 and 39 are tucked in around the interior of the primary insert 20.

Figure 2:
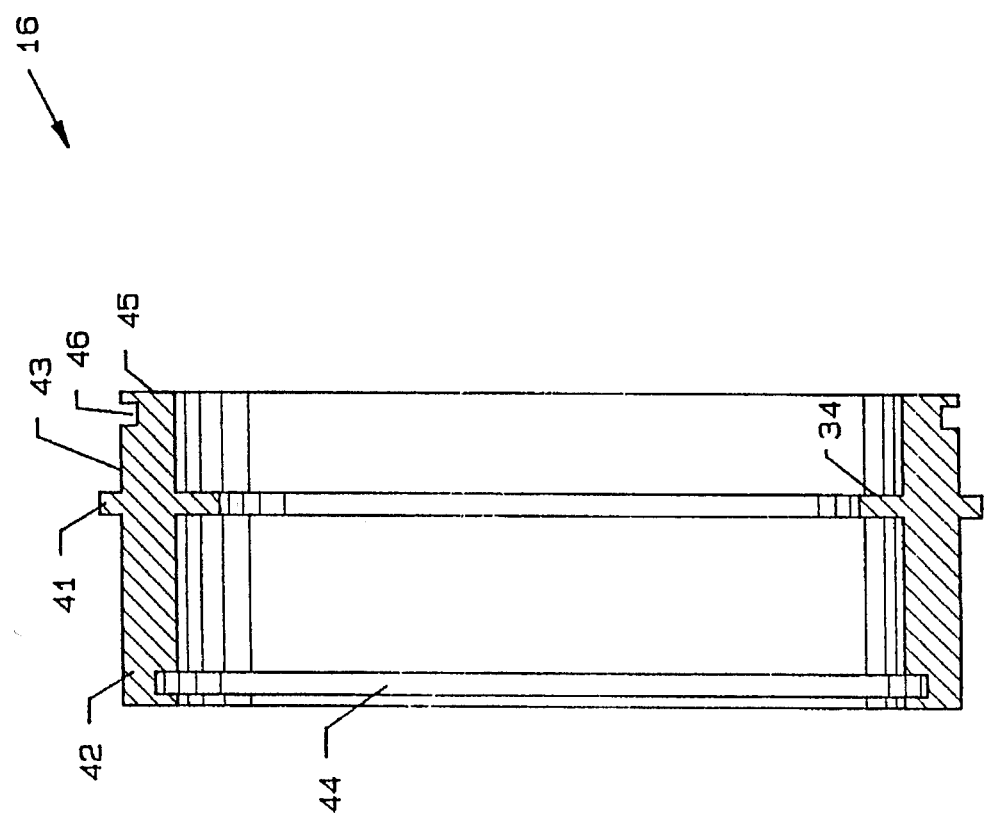
FIG. 2 illustrates a cross sectional view of the cylinder adaptor.

FIG. 2 illustrates a cross sectional view of the cylinder adaptor 16, including an outer rim 41, a cylindrical surface 43, a cylindrical portion 42, an inner O-groove 44 on the inner surface of the cylindrical portion 42, an annular surface 45, and an outer O-ring groove 46 on the cylindrical surface 43. The inner O-groove 44 receives and O-ring 22 illustrated in FIG. 1 and the outer O-ring groove 46 receives an O-ring 24 illustrated in FIG. 1. The O-ring 22 in the inner O-groove 44 seals against the outer surface 33 of the VCS cylinder 32 and the O-ring 24 seals against the inner surface of the housing 12 as illustrated in FIG. 1.

Figure 3:
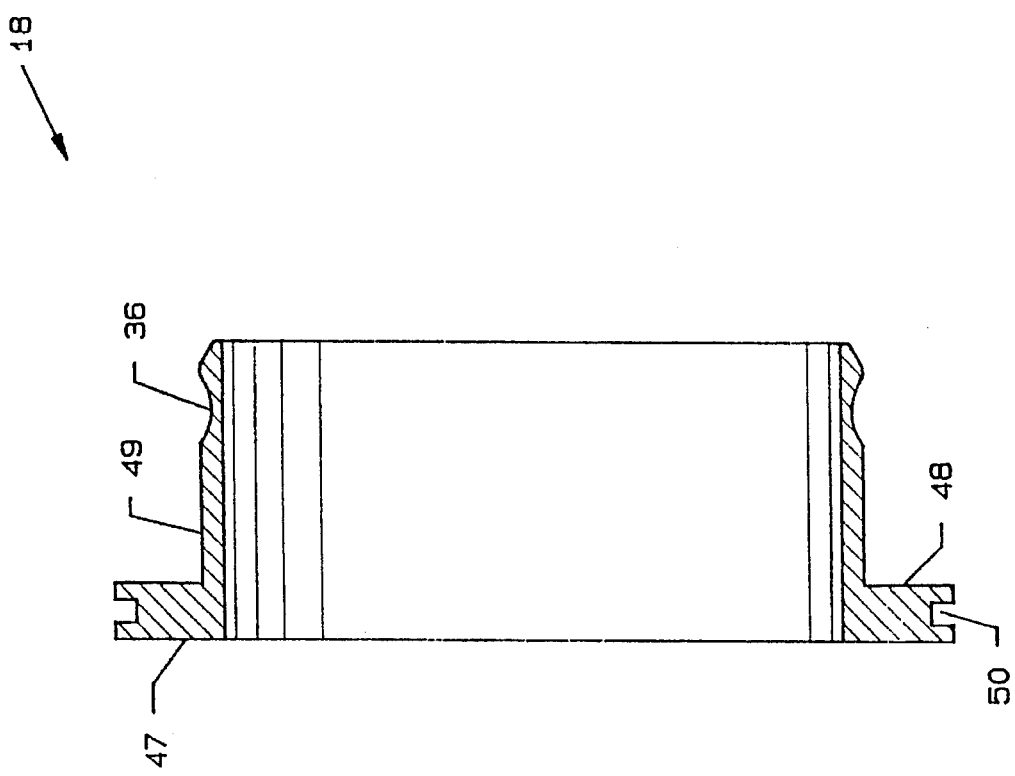
FIG. 3 illustrates a cross sectional view of the piston.

FIG. 3 illustrates a cross sectional view of the piston 18, including the constriction ring groove 36 in a cylindrical portion 49, an annular surface 47, an outer rim 48, and an O-ring groove 50 for the O-ring 26 of FIG. 1 where all numerals correspond to those previously described.

Figure 4:
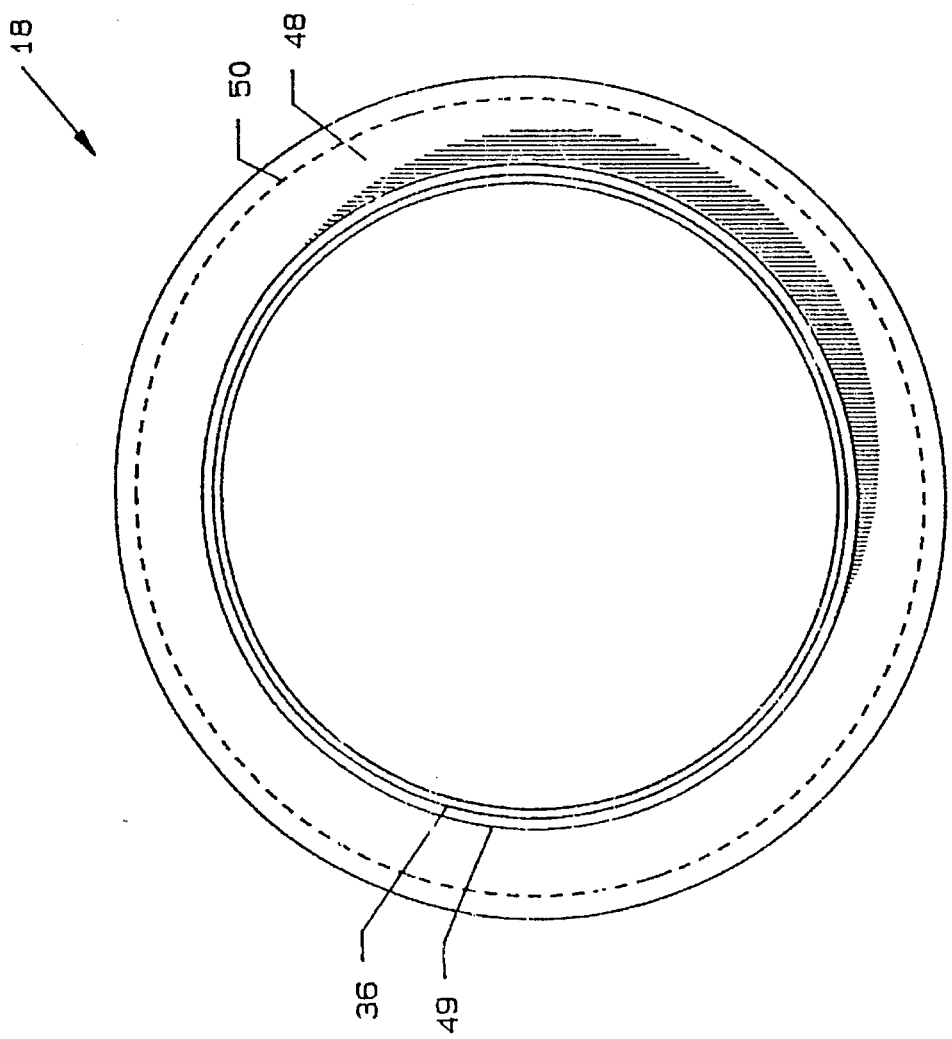
FIG. 4 illustrates a right end view of the piston.

FIG. 4 illustrates a right end view of the piston 18 where all numerals correspond with those once previously identified.

Figure 5:
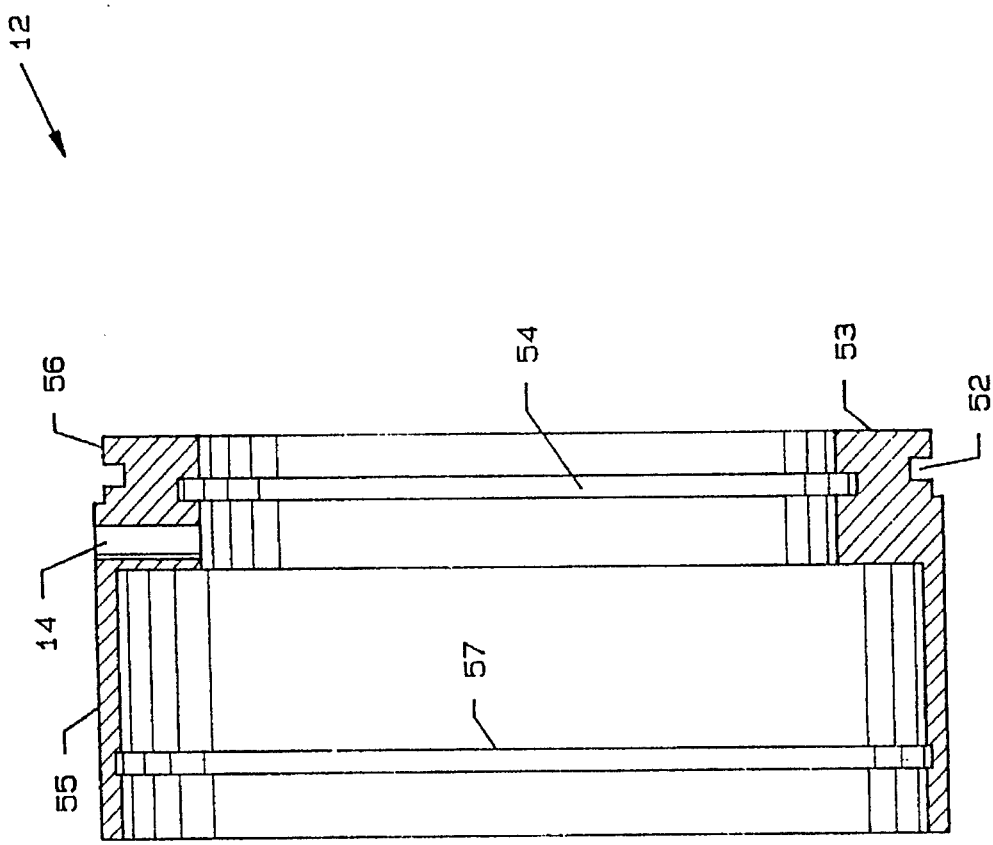
FIG. 5 illustrates a cross sectional view of the housing.

FIG. 5 illustrates the housing 12, including external and internal O-ring grooves 52 and 54 respectively, and the vent 14 where all numerals correspond to those elements previously described. A cylindrical portion 55 extends longitudinally and includes an O-ring groove 57 on its inner surface. The cylindrical surface 56 receives the lip 58 of the primary insert 20 of FIG. 7. The O-ring groove 57 on the inner surface of the housing 12 accommodates O-ring 24 illustrated in FIG. 1. O-ring 24 provides a seal between the housing 12 and the cylindrical adaptor 16. An annular surface 53 intersects the cylindrical surface 56 and is used to force the constriction ring 38 from the groove 36 illustrated in FIG. 1 as later described in detail.

Figure 6:
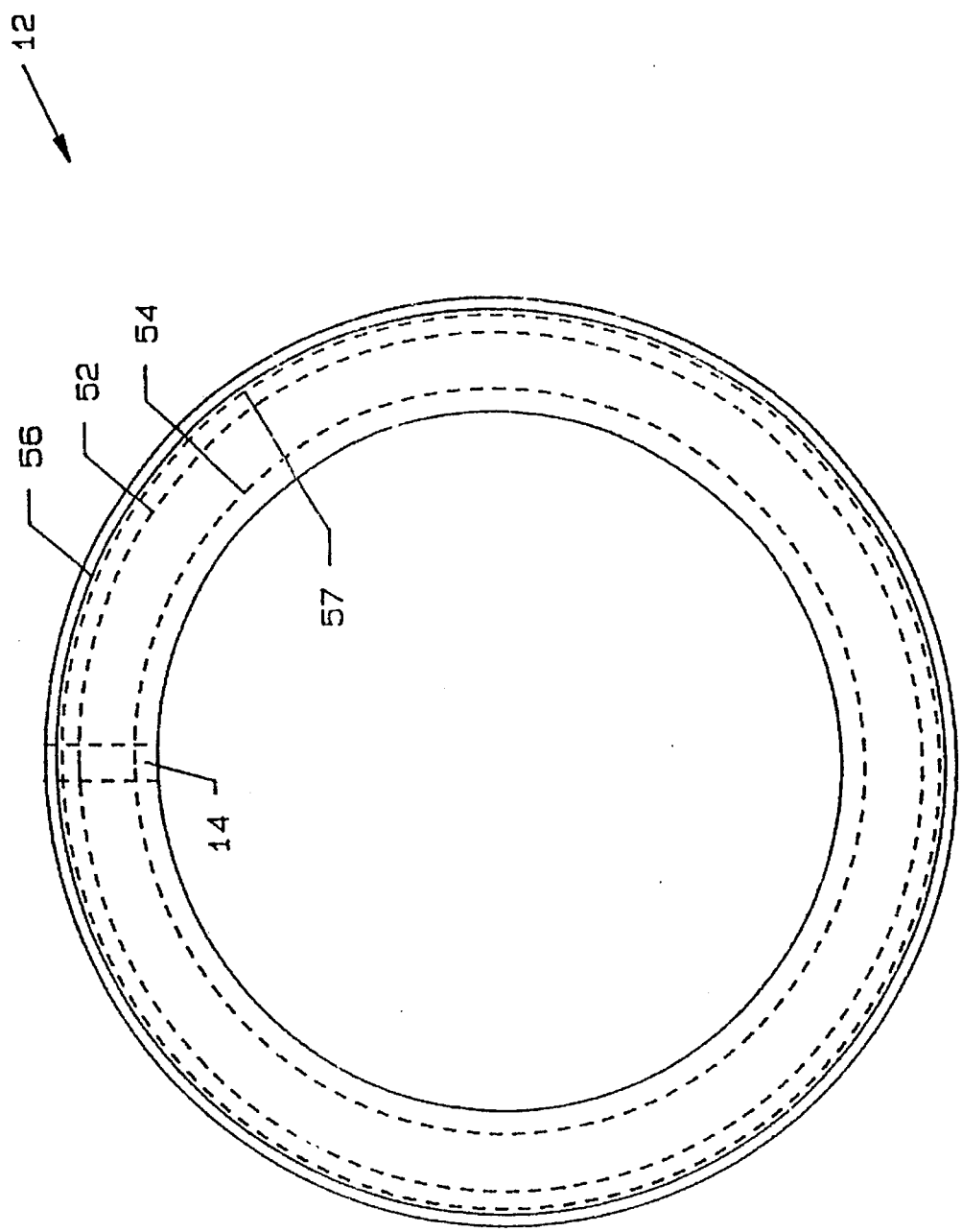
FIG. 6 illustrates a right end view of the housing.

FIG. 6 illustrates the right end view of FIG. 5 where all numerals correspond with those once previously described.

Figure 7:
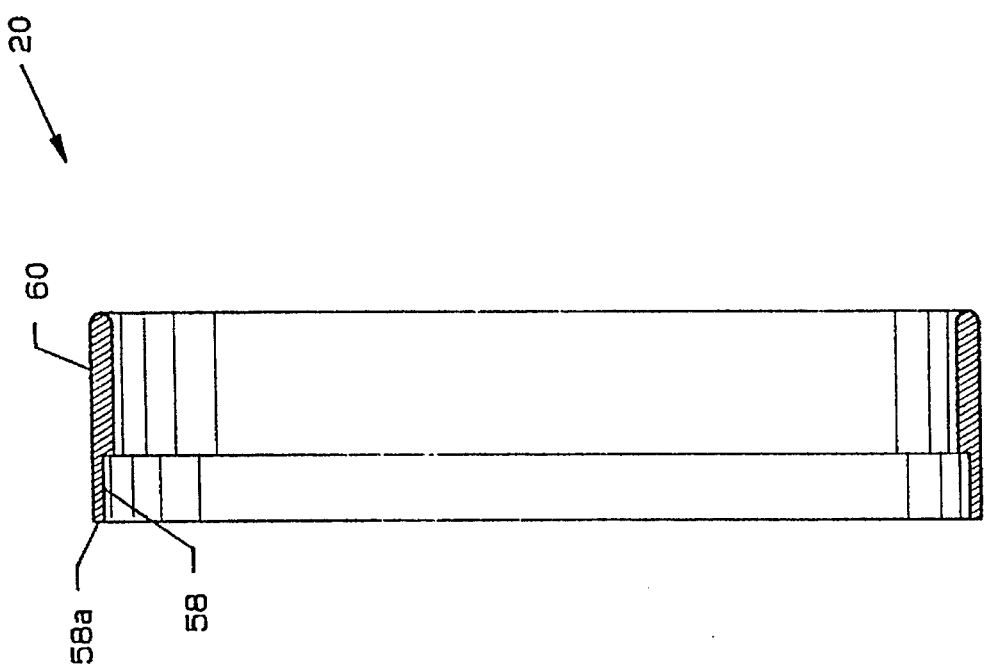
FIG. 7 illustrates a cross sectional view of the primary insert.

FIG.7 illustrates the primary insert 20, including the lip 58 with a sealing surface 58a and cylindrical portion 60 where all numerals correspond to those elements previously described. The primary insert can be made of a soft pliable material for engaging soft pliable elastomeric polymer for engaging with the body and forming an airtight seal for the vacuum constriction system so that a vacuum can be drawn aiding the penile erection.

Figure 8:
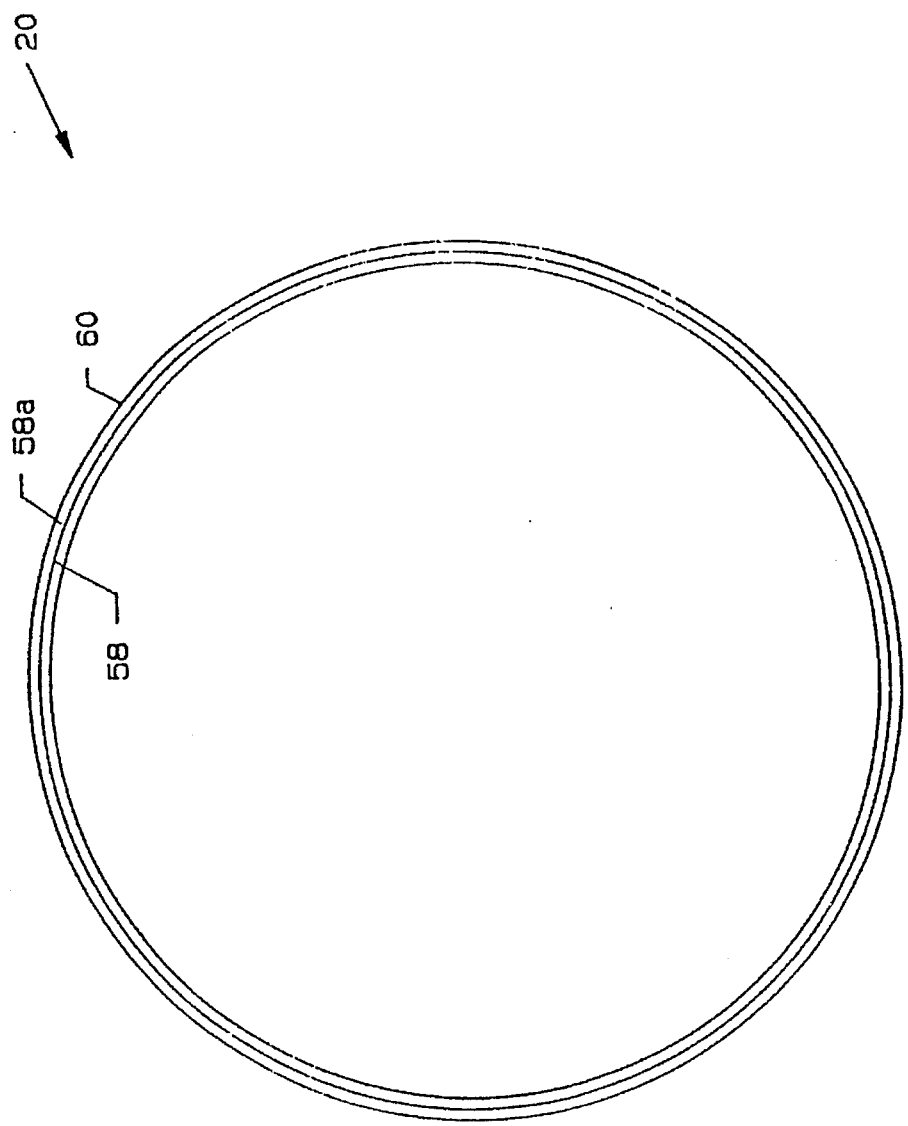
FIG. 8 illustrates a left end view of the insert.

FIG. 8 illustrates a left end view of FIG. 7 where all numerals correspond to those elements previously described.

MODE OF OPERATION

Figure 9:
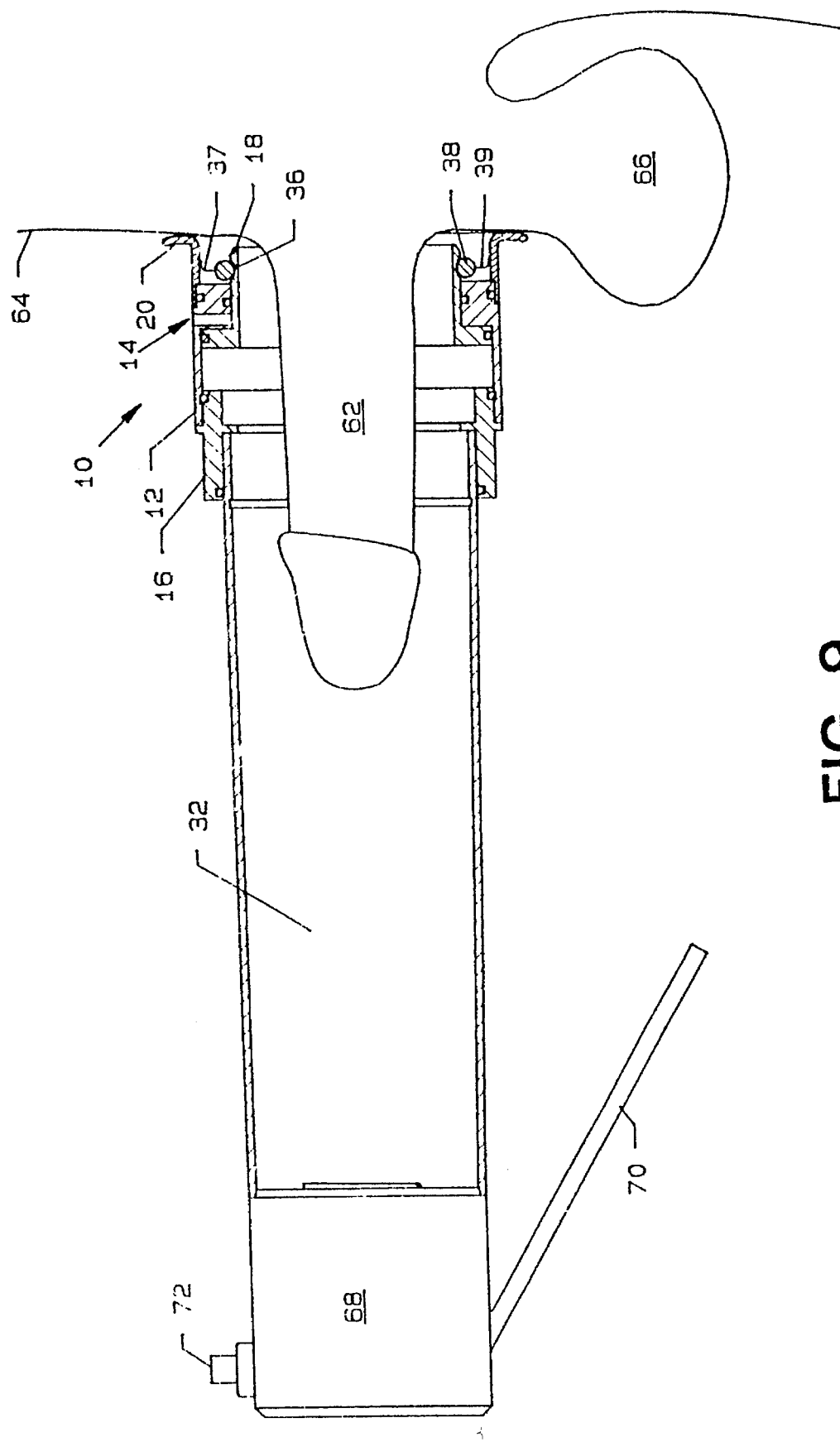
FIG. 9 illustrates a mode of operation with a constriction ring loaded on the piston and about the base of the penis and engaged up against the body.

FIG. 9 illustrates a internal ring releasing device 10 for vacuum constriction system in an as-loaded and in use where all numerals correspond to those elements previously described. The internal ring releasing device 10 is placed over a flaccid penis 62 and brought into mild but firm contact with the abdomen 64 and against the scrotum 66 in order to form a seal. A suitable vacuum pump 68 such as the "Mentor Response Head" including a vacuum pump lever 70 and air release valve 72, is actuated to create a vacuum about the flaccid penis 62 and within the VCS chamber 32 after first placing one's finger or other object over the vent hole 14.

Figure 10:
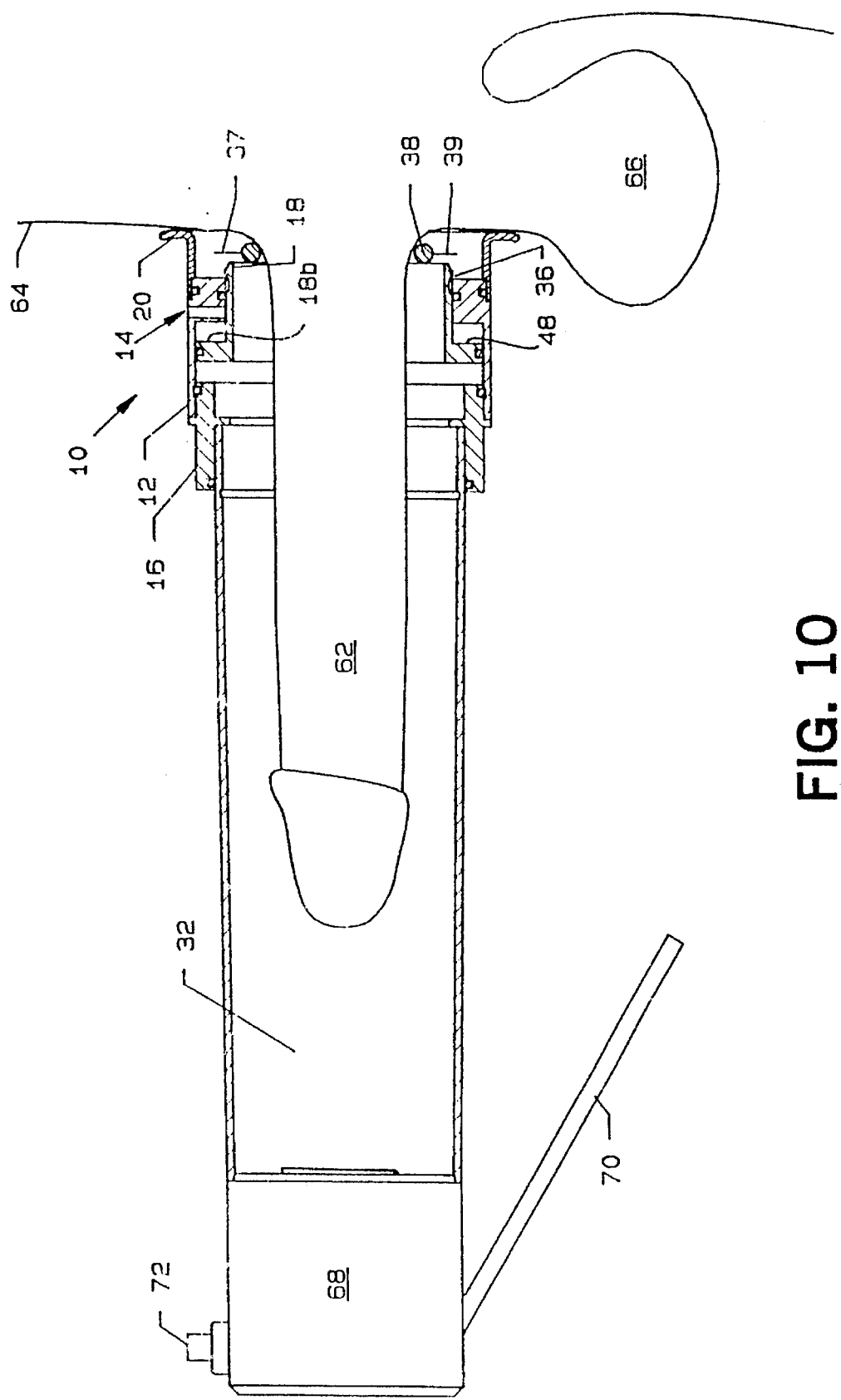
FIG. 10 illustrates the constriction ring unloaded about the base of the erect penis.

FIG. 10 illustrates the internal ring releasing device 10 for vacuum constriction system in an unloaded state where the piston 18 is withdrawn and the constriction ring 38 is about the base of a penis 62 providing for quality erection where all numerals correspond to those elements previously described.

After a penis erection is accomplished the vent 14 is uncovered thus causing the piston 18 to move distally forcing the constrictor ring 38 from the groove 36 and also from the piston 18 to deposit the constrictor ring 38 around and about the base of the penis 62. A relatively positive pressure is introduced along the outer rim 48 by opening of the vent 14 to ambient atmospheric pressure. Sufficient clearance between the cylindrical portion 49 of the piston and cylindrical surface 56 of the housing 12 ports ambient pressure to the outer rim 48 of the piston 18. The piston 18 is moved by the relatively high ambient pressure into the relatively low pressure area on the distal side of the outer rim 48 to dislodge the constrictor ring 38. The vacuum pump 68 is then deactivated and removed along with the internal ring releasing device 10.

The steps for operation are now set forth.

1. Remove the primary insert 20, using a slight rotational force.

2. Pull out the piston 18 to the maximum extended position.

3. Place the internal ring releasing device on flat surface 10, lubricate the internal ring releasing device piston ridge, and stretch the vacuum constriction system constriction ring 38 over the piston 18.

4. Replace the primary insert 20, slightly rotating into place to ensure the ears 37 and 39 of the constriction ring 38 are free and loose.

5. Attach the vacuum constriction system cylinder tube 32 to the cylinder adaptor 16 of the internal ring releasing device 10.

6. Place the assembly 10 over penis. Use the index finger to cover the vent 14 which is located on the housing 12 sidewall.

7. Begin to pull a vacuum until an adequate erection is obtained and then remove finger from vent 14.

8. The constriction ring 38 will be released about the base of the penis as the negative pressure differential causes the piston 18 to retract.

9. Press air release valve 72 and remove assembly from penis base.

FIRST ALTERNATIVE EMBODIMENT

Figure 11:
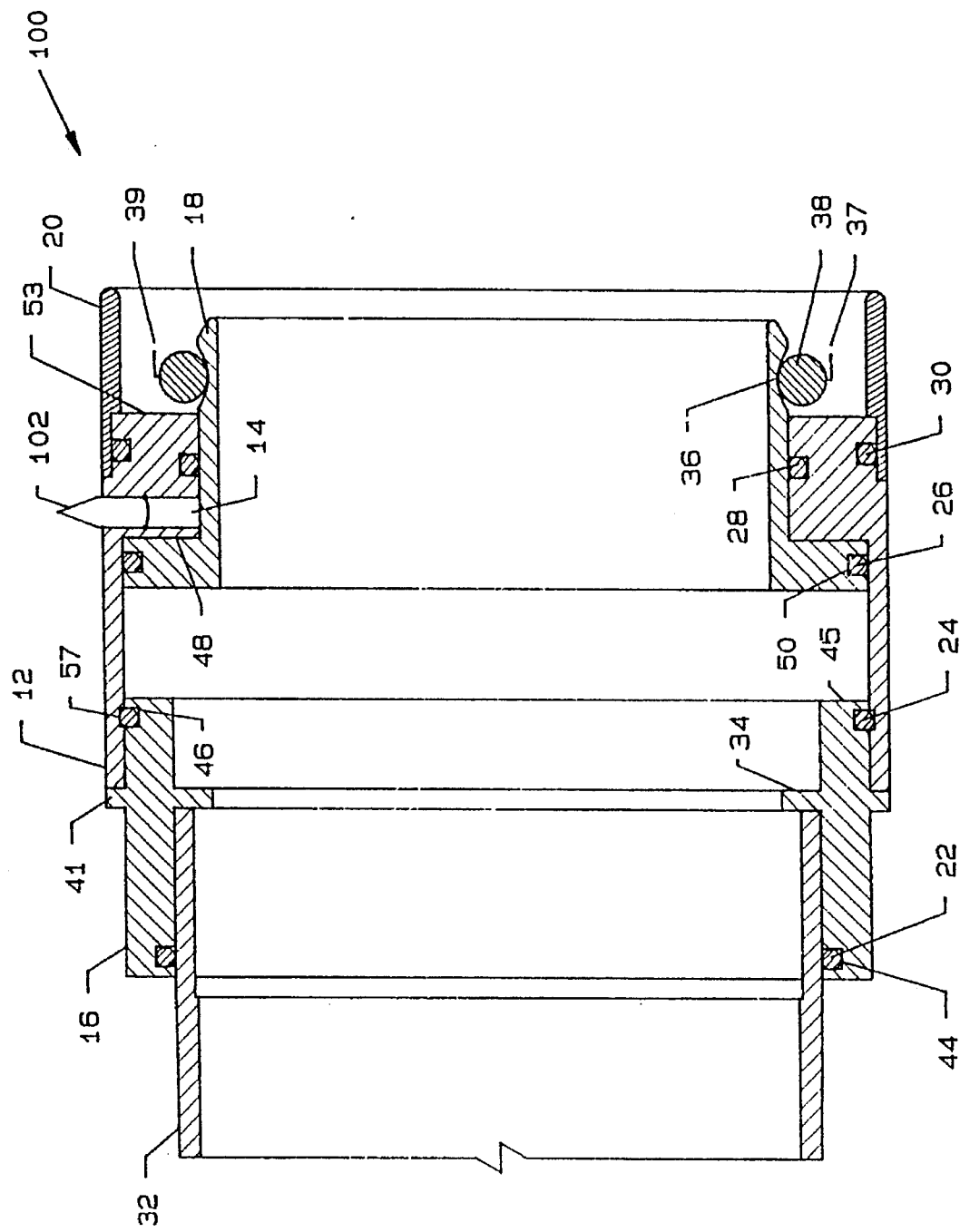
FIG. 11 illustrates a cross sectional view of a first alternative embodiment with an elastomeric valve.

FIG. 11 illustrates a cross sectional view of a first alternative embodiment of an internal ring releasing device 100 where all numerals correspond to those elements previously described and including an elastomeric deflecting valve 102 aligned in the vent 14. The internal ring releasing device 100 is similar to the internal ring releasing device 10 but also includes the elastomeric deflecting valve 102. The particular valve 102 is an elastomeric deflecting valve which provides for release of pressure when the valve 102 is depressed to the side at the proper time and does not require constant sealing of the vent 14 by one's finger.

SECOND ALTERNATIVE EMBODIMENT

Figure 12:
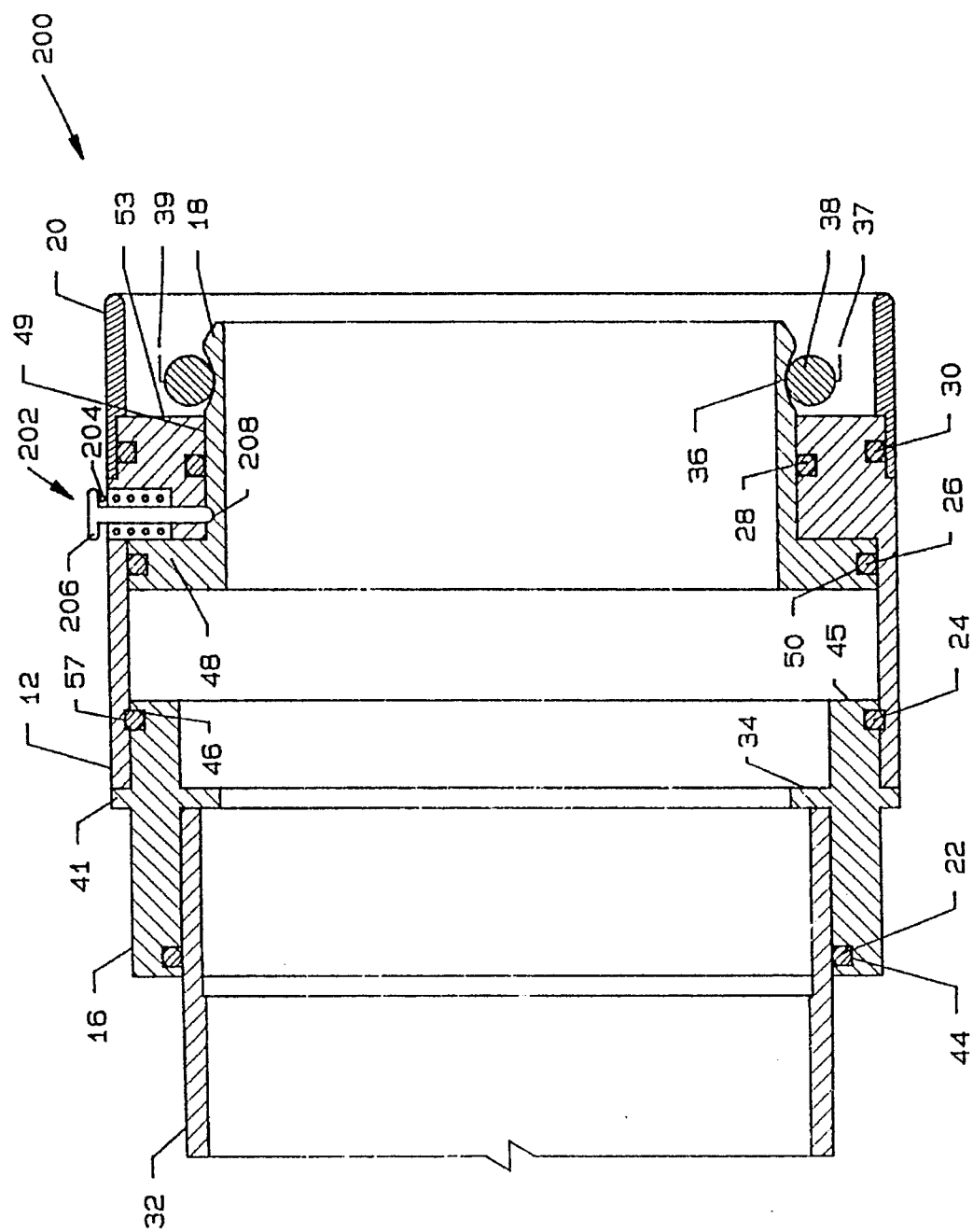
FIG. 12 illustrates a cross sectional view of a second alternative embodiment with a mechanical valve.

FIG. 12 illustrates an internal ring releasing device 200 for a vacuum constriction device similar in construction to the internal ring releasing device 10, but including a mechanical release 202 consisting of a spring 204 and plunger 206 located in the position where the vent 14 was previously located where all numerals correspond to the elements previously described. Additionally, an annular groove 208 is included on the outer surface cylindrical portion 49. The plunger 206 is manually depressed to engage the annular groove 208 thus holding the piston 18 immovable until such time that it is deemed necessary to retract the plunger 206 allowing the piston 18 to move distally thus dislodging the constriction ring 38 from the groove 36 to a position around and about the base of the penis. Outward movement of the plunger 206 also allows ambient air to be vented to the outer rim 48 of the piston thus causing the piston 18 to move in a distal direction. Thus plunger depressing mechanically and pneumatically releases the piston 18 to provide movement of the piston 18 once a negative pressure is created by the VCD system.

THIRD EMBODIMENT ALTERNATIVE

Figure 13:
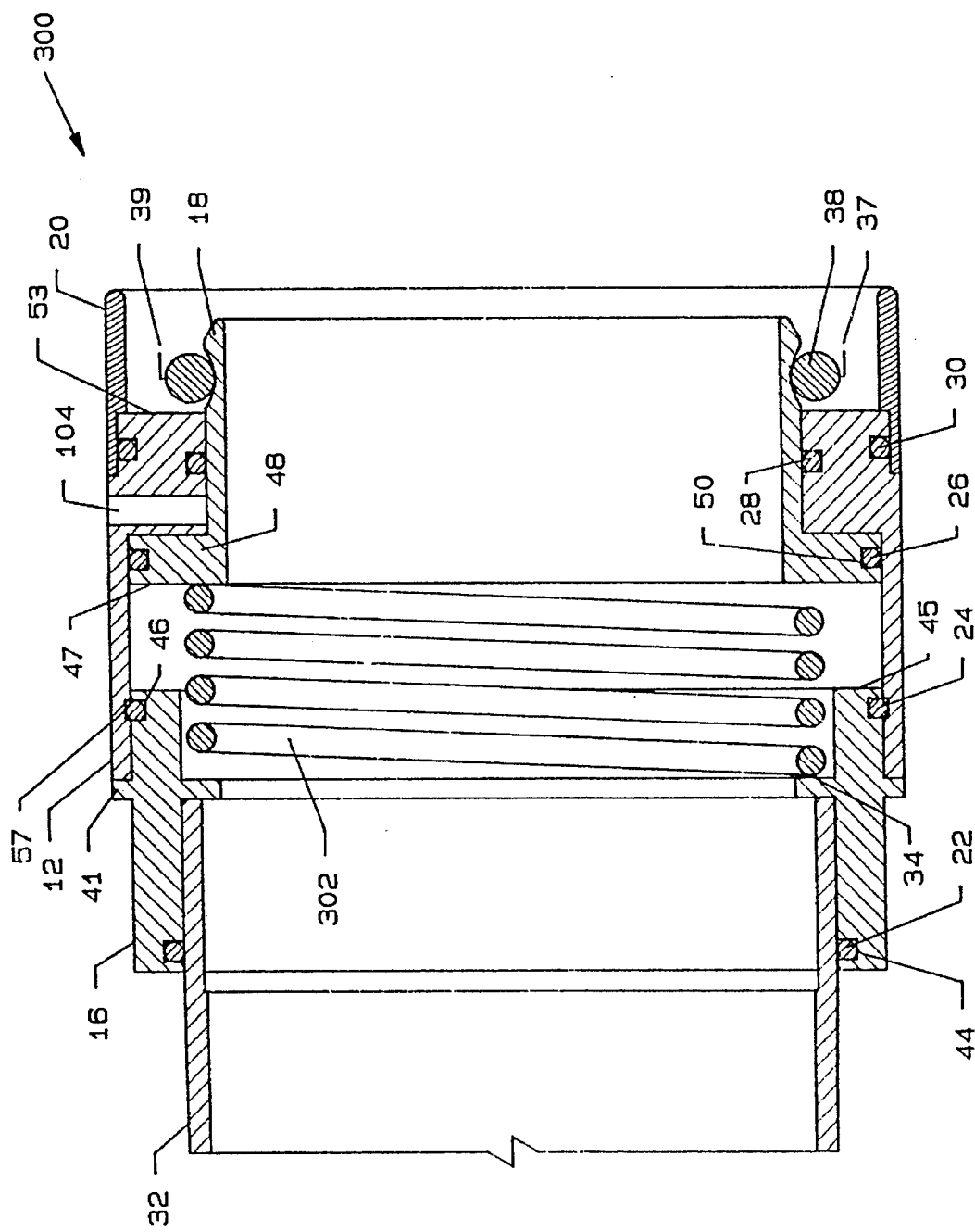
FIG. 13 illustrates a cross sectional view of a third alternative embodiment with an internally located spring.

FIG. 13 illustrates an internal ring releasing device 300 for a vacuum constriction device similar in construction to the internal ring releasing device 10, but including a spring 302 placed between the annular surface 47 of the piston 18 and the rim 34 of the cylinder adaptor 16. When the vent 14 is opened, be it a simple vent such as vent 14, an elastomeric deflecting valve 102 and vent 104 combination, a mechanical release 202 or other suitable vent release, sufficient vacuum must be applied to cause the piston 18 to overcome the force of the spring 302 to allow the piston 18 to traverse distally to dislodge the constrictor ring 38 from the piston 18. The spring 302 can be of different desired strengths to accommodate variable factors such as vacuum, constrictor ring size elasticity and the like. The spring 302 also assists in returning the piston 18 to the reload position.

FOURTH ALTERNATIVE EMBODIMENT

Figure 14:
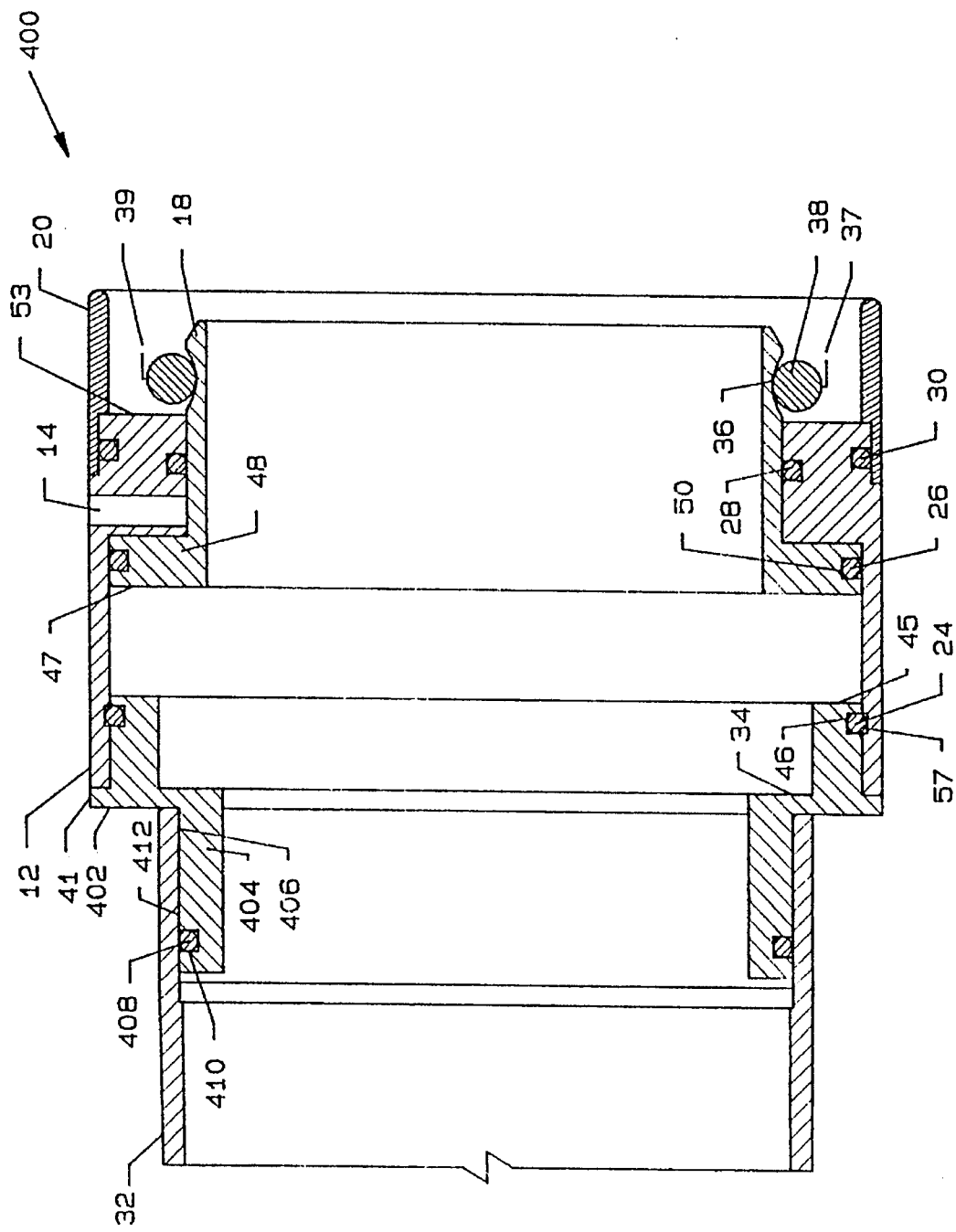
FIG. 14 illustrates a cross sectional view of a fourth alternative embodiment where a modified cylinder adaptor fits to and is accommodated by the interior surface of a VCS cylinder.

FIG. 14 illustrates an internal ring releasing device 400 for a vacuum constriction device similar in construction to the internal ring releasing device 10, but including a modified cylinder adaptor 402 having a necked down cylindrical portion 404 which is appropriately sized to accommodate the inner surface 406 of the VCS cylinder 32 instead of the outer surface 33 as depicted in previous figures. An O-ring 408 in an O-ring groove 410 seals the inner surface 406 of the cylinder adaptor 402 to the outer surface 412 of the necked down cylindrical portion 404. Any suitable vent closure such as a finger over the vent 14, an elastomeric deflecting valve 102, a mechanical release 202, or any other suitable vent relief or closure, or spring 204 may be incorporated in the use of the internal ring releasing device 400.

FIFTH ALTERNATIVE EMBODIMENT

Figure 15:
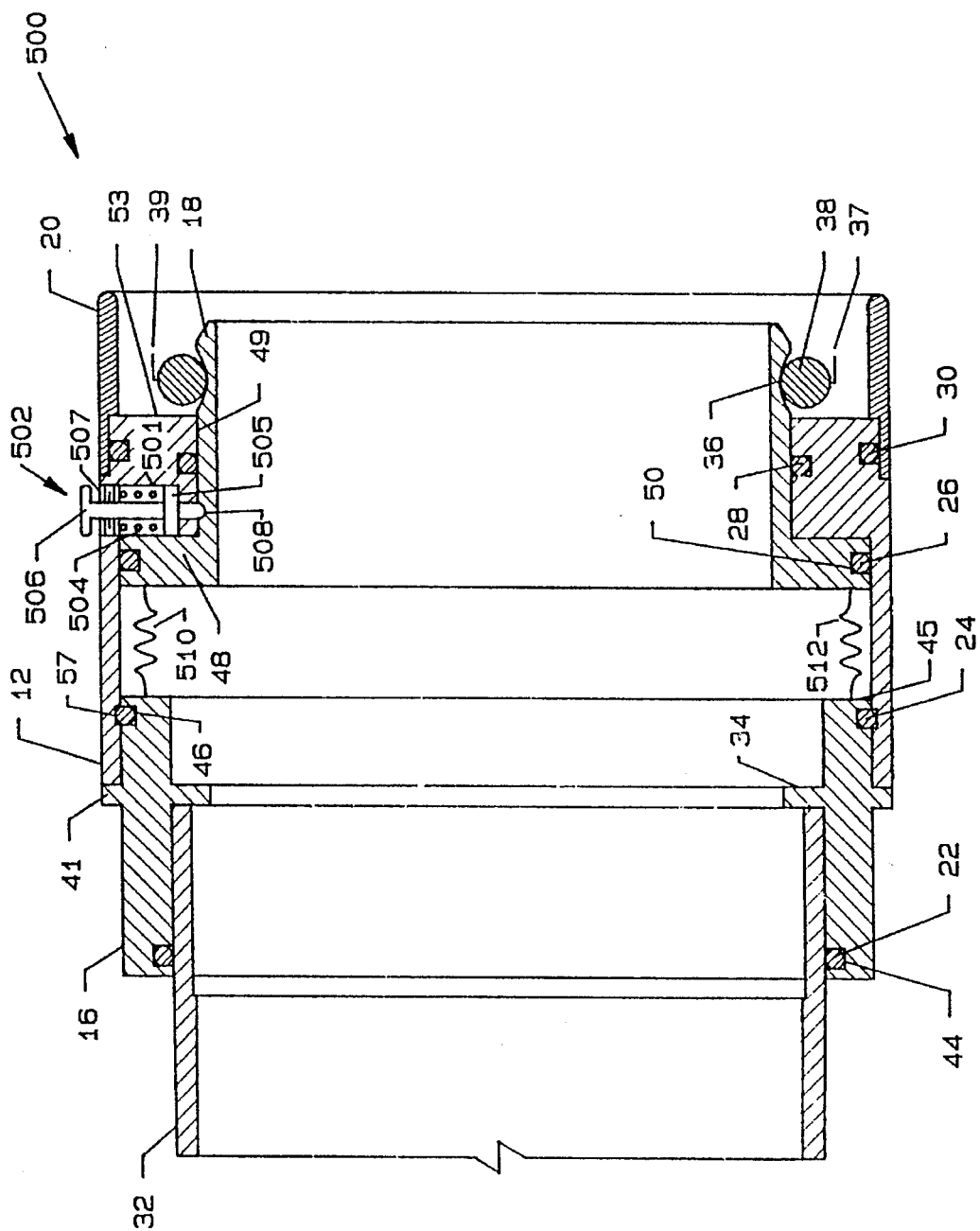
FIG. 15 illustrates a cross sectional view of a fifth alternative embodiment having tension springs aligned between the cylinder adaptor and the piston for mechanical piston actuation.

FIG. 15 illustrates an internal ring releasing device 500 similar to that previously described in FIG. 12 for a vacuum constriction device similar in construction to the internal ring releasing device 10, and including tension springs which mechanically position the piston 18 in the event that vacuum is not incorporated for piston actuation. Tension springs 510 and 512 suitably secure between the annular surface 45 of the cylinder adaptor 16 and the annular surface 47 of the piston 18 to provide for movement of the piston 18 in a distal direction. Also included is a mechanical release 502 consisting of a spring 504 aligned about a plunger 506 located in a cavity 501 in the position where the vent 14 was previously located where all numerals correspond to the elements previously described. An annular disk-like shouldered member 505 is located on the lower portion of the plunger 506. A threaded insert 507 aligns and secures in the housing 12 to capture the spring 504 between the threaded insert 507 and the shouldered member 505. The spring 504 insures engagement of the plunger 506 with an annular groove 508 included on the outer surface cylindrical portion 49 of the piston 18. Actuation of the plunger 506 in an outward direction and overcoming the spring tension 504 allows movement of the plunger 18 distally. The plunger 506 normally engages the annular groove 508 by the compression spring 504 thus holding the piston 18 immovable until such time that it is deemed necessary to retract the plunger 506 allowing the piston 18 to move by force of springs 510 and 512 distally thus dislodging the constriction ring 38 from the groove 36 to a position around and about the base of the penis.

SIXTH ALTERNATIVE EMBODIMENT

Figure 16:
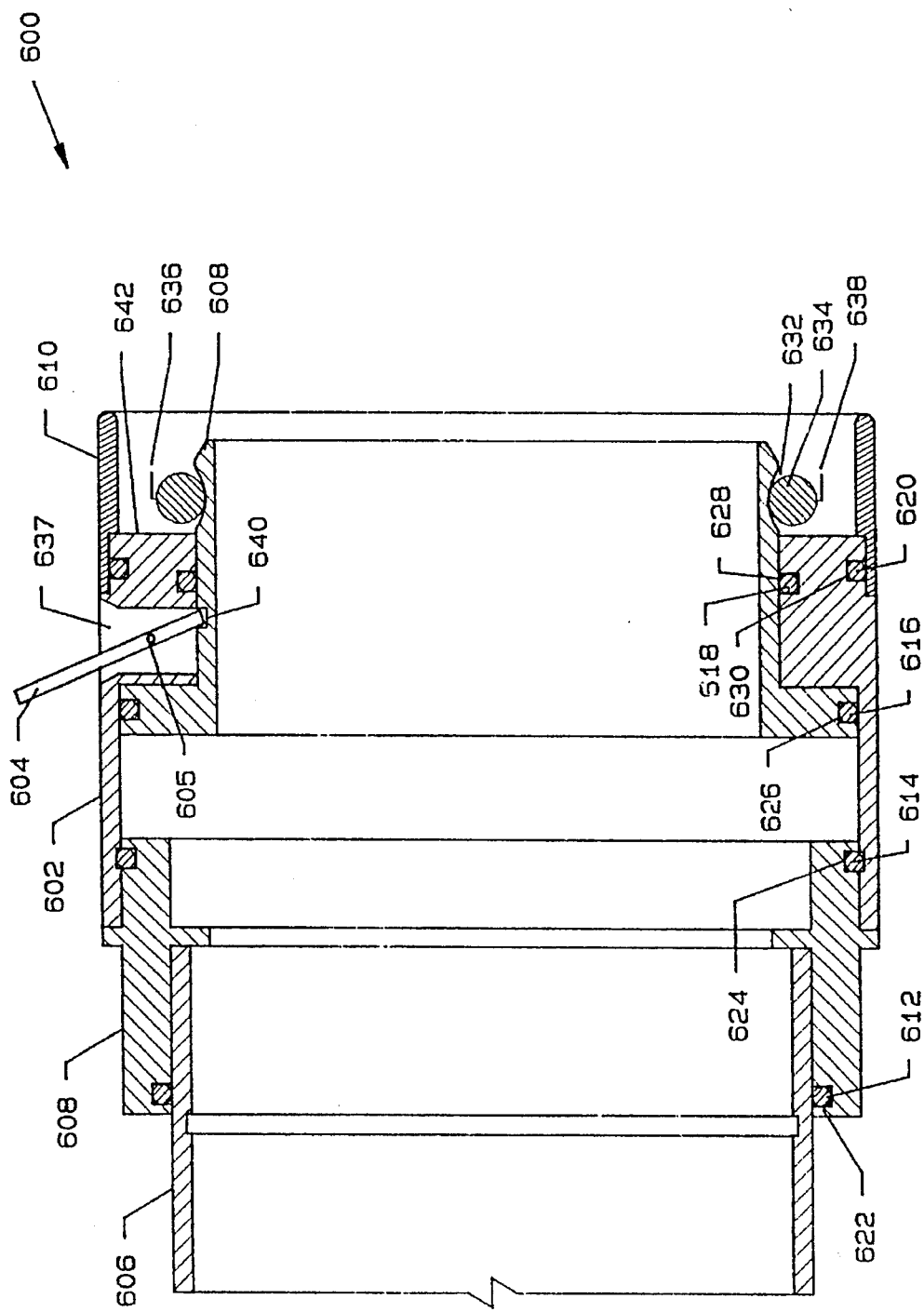
FIG. 16, a sixth alternative embodiment, illustrates a cross sectional view having a lever operator which positions the piston to the load position as illustrated.

FIG. 16 illustrates a cross sectional view of a manually operated internal ring releasing device 600 including a housing 602, a pivoting lever operator 604, a pin 605 secured into the housing 602 and residing in a cavity 637, a cylinder adaptor 606, a piston 608, and an optional primary insert 610. A plurality of O-rings 612, 614, 616 and 620 align in O-ring grooves 622, 624, 626, 628 and 630 respectively in the above members to provide appropriate sealing of surfaces without and within as previously described in previous FIGS. A groove 632, on the piston 608, receives a constriction ring 634 having ears 636 and 638 which are tucked around the interior of the primary insert 610. The lever operator 604 aligns in and pivots within a cavity 637 and pivots about the pin 605 in the housing 602 to position the piston 608 to the load positions as illustrated or to the unload position illustrated in FIG. 17. A cavity 640 on the outer surface of the piston 608 engages the inboard end of the pivoting lever operator 604 to provide for manual positioning of the piston 608.

Figure 17:
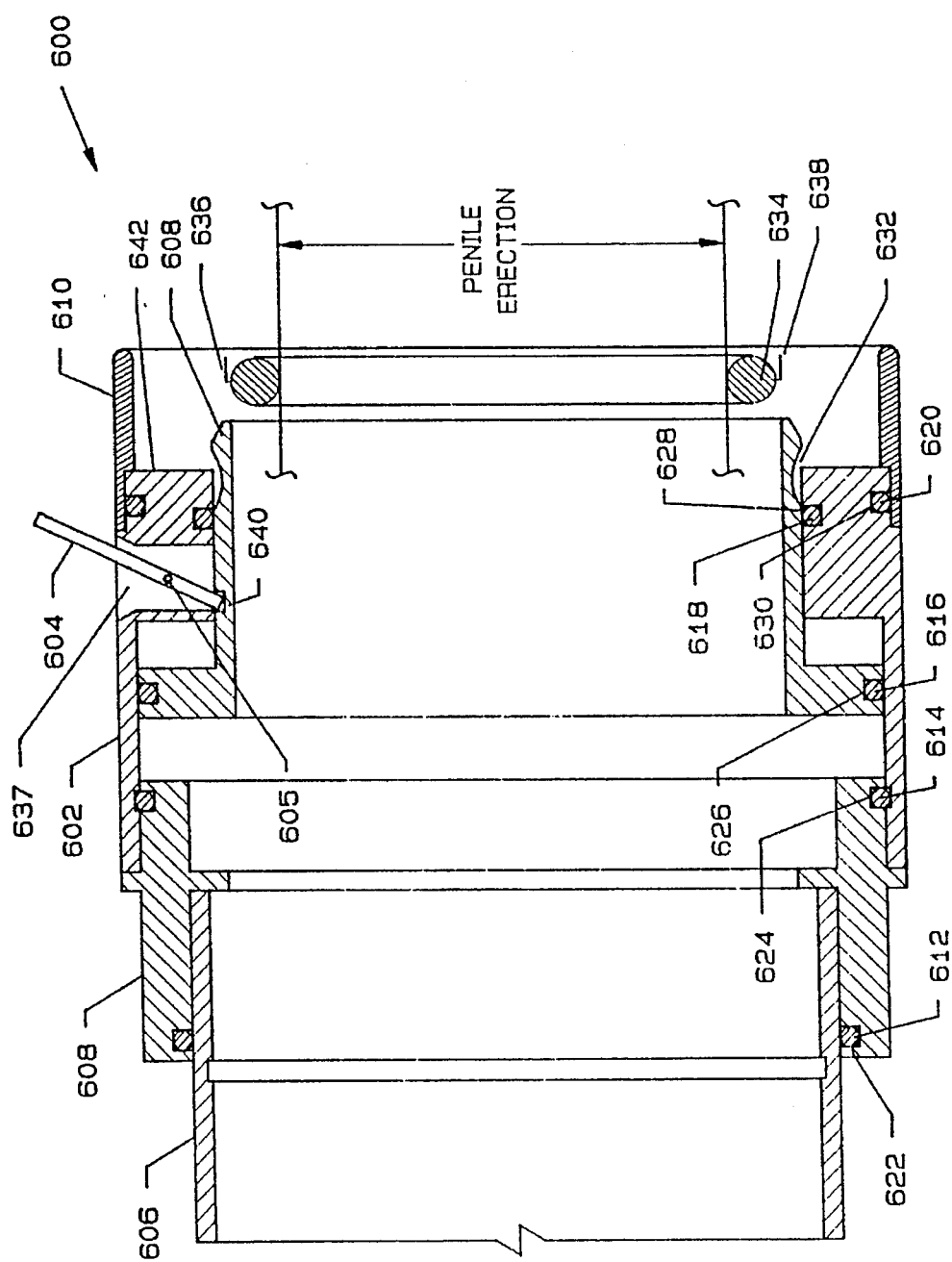
FIG. 17 illustrates the internal ring releasing device of FIG. 16 in the unloaded position.

FIG. 17 illustrates the internal ring releasing device 600 released from the piston 608 and about the base of penile erection which is not fully illustrated. All numerals correspond to those previously described. As the piston 608 is positioned distally by operation of the lever operator 604 the constriction ring 634 is dislodged from the piston 608 by the annular surface 642 of the housing 602 to be placed about the base of the penis.

Various modifications can be made to the present invention without departing from the apparent scope hereof. The IRRD can be constructed of any suitable polymer such as a clear or opaque material. The cylinder of the VCD and the IRRD can be constructed as an integral unit.

I claim:

1. An internal ring release device (IRRD) comprising:
   a. a cylindrical housing;
   b. a piston slidably engaged into said housing and including an outer rim engaging an inner wall of said housing;
   c. means for supporting a constriction ring at one end of said piston and internal to said cylindrical housing; and,
   d. means for causing said piston to move from a first position to a second position whereby said constriction ring thereby slides off said end of said piston about a base of a penile erection.

2. The IRRD of claim 1 wherein said movement means is a lever means affixed to said piston through said housing.

3. The IRRD of claim 1 wherein said movement means comprising:
   a. a tension spring means; and,
   b. a pin means between said housing and said piston whereby said pin means provides for positioning of said constriction ring.

4. The IRRD of claim 1 wherein said movement means is a vacuum means.

5. The IRRD of claim 4 including a vent hole through said housing.

6. The IRRD of claim 5 including an elastomeric valve in said vent hole.

7. The IRRD of claim 5 including a mechanical valve in said vent hole.

8. The IRRD of claim 5 including an automatic valve in said vent hole.

9. The IRRD of claim 4 including a spring between said piston and said housing whereby said spring limits minimum vacuum for movement of said piston and release of said constriction ring.

10. The process for releasing a constriction ring from an internal ring releasing device (IRRD) comprising the steps of:
    a. placing a constriction ring on an end of a slidable piston of an internal ring releasing device;
    b. mating a vacuum constriction device (VCD) to said IRRD;
    c. creating a vacuum with said VCD about a penis; and,
    d. causing said piston to move whereby said ring slides off of said end of said piston about a base of a penile erection.

* * * * *